United States Patent
Helton et al.

(10) Patent No.: US 10,478,438 B2
(45) Date of Patent: Nov. 19, 2019

(54) TREATMENT OF ORGANOPHOSPHATE EXPOSURE WITH OCINAPLON

(76) Inventors: David Reed Helton, Dana Point, CA (US); Ernest Pfadenhauer, Santa Barbara, CA (US)

(*) Notice: Subject to any disclaimer, the term of this patent is extended or adjusted under 35 U.S.C. 154(b) by 302 days.

(21) Appl. No.: 13/124,366

(22) PCT Filed: Oct. 16, 2009

(86) PCT No.: PCT/US2009/061091
§ 371 (c)(1),
(2), (4) Date: Jun. 22, 2011

(87) PCT Pub. No.: WO2010/045615
PCT Pub. Date: Apr. 22, 2010

(65) Prior Publication Data
US 2011/0245275 A1    Oct. 6, 2011

Related U.S. Application Data

(60) Provisional application No. 61/106,125, filed on Oct. 16, 2008.

(51) Int. Cl.
*A61K 31/519* (2006.01)
(52) U.S. Cl.
CPC .................. *A61K 31/519* (2013.01)
(58) Field of Classification Search
CPC .................................................. A61K 31/519
See application file for complete search history.

(56) References Cited

U.S. PATENT DOCUMENTS

| | | |
|---|---|---|
| 3,761,479 A | 9/1973 | Hoffman et al. |
| 4,169,948 A | 10/1979 | Dunbar et al. |
| 4,382,938 A | 5/1983 | Kaplan et al. |
| 4,521,422 A | 6/1985 | Duaza et al. |
| 4,626,538 A | 12/1986 | Duaza et al. |
| 6,399,621 B1 | 6/2002 | Duaza et al. |
| 2002/0058669 A1 | 5/2002 | Van Helden et al. |
| 2003/0013726 A1 | 1/2003 | Selzer |
| 2008/0045547 A1 | 2/2008 | Lippa et al. |
| 2008/0200473 A1 | 8/2008 | Falco et al. |
| 2008/0287463 A1 | 11/2008 | Herrmann et al. |

OTHER PUBLICATIONS

Volans (J Acad Emerg Med 1996 13, 202-206) in view of Lippa et al. (PNAS, 102, 20, 7380-7385).*
Lippa et al. (PNAS, 102, 20, 7380-7385).*
Lee et al. (JAMA 2003, 290, 659-662).*
International Search Report and Written Opinion, International Patent Application No. PCT/US2009/061091, dated May 28, 2010.
International Preliminary Examination Report, International Patent Application No. PCT/US2009/061091.
Lacy, T. J. et al., Terrorism and weapons of mass destruction: managing the behavioral reaction in primary care. Southern Medical J. Apr. 2003;96(4): pp. 394-399 (Abstract).

* cited by examiner

*Primary Examiner* — Umamaheswari Ramachandran
(74) *Attorney, Agent, or Firm* — Loza & Loza, LLP; Michael F. Fedrick

(57) ABSTRACT

A method of treating exposure to organophosphate agents and preventing morbidity due to such exposure through the administration of a pyrazolopyrimidine compound such as ocinaplon, zaleplon, indiplon, or divaplon.

8 Claims, No Drawings

TREATMENT OF ORGANOPHOSPHATE EXPOSURE WITH OCINAPLON

CROSS-REFERENCE TO RELATED APPLICATIONS

This application is the U.S. national stage of International Patent Application No. PCT/US09/61091, filed on Oct. 16, 2009 and entitled TREATMENT OF ORGANOPHOSPHATE EXPOSURE WITH OCINAPLON, which claims the benefit of priority from U.S. Patent Application No. 61/106,125, filed Oct. 16, 2008. The disclosures of the foregoing applications are incorporated herein by reference in their entirety.

BACKGROUND

Organophosphate compounds, in particular organic esters of substituted phosphoric acids, have been developed for use as chemical weapons. These compounds inhibit cholinesterases and disrupt the peripheral nervous system by preventing these enzymes from breaking down acetylcholine. Some organophosphate compounds are sufficiently potent that even brief exposure may be fatal.

Organophosphate anticholinesterase agents include tabun (Ethyl N,N-dimethylphosphoramidocyanidate, also referred to as GA), sarin (O-Isopropyl methylphosphonofluoridate, also referred to as GB), soman (O-Pinacolyl methylphosphonofluoridate, also referred to as GD), and VX (O-ethyl-S-[2(diisopropylamino)ethyl]methylphosphonothiolate). Tabun, sarin, and soman in particular are highly volatile and easily disseminated in vapor form. They are also readily absorbed through the lungs, eyes, skin, and intestinal tract.

Present treatments for organophosphate exposure include the administration of anticholinergic agents such as atropine and glycopyrrolate, as well as agents such as pralidoxime (2-PAM) that prevent the aging of AChE and that reverse muscle paralysis. Diazepam, a benzodiazepine, can also be administered to treat organophosphate exposure.

The present treatments for organophosphate exposure, however, do not completely treat the effects of such exposure, and in addition are associated with unwanted side effects. In view of this and of the threat posed by organophosphate agents, improved therapies for treating individuals exposed to such agents and for preventing the harm that these agents can cause are needed.

SUMMARY

The potential personal and health care burden from an organophosphate attack underscores the need for effective treatments that will not only increase the survival of individuals exposed to such agents but will also provide protection from the long-term health consequences of exposure, since low-level exposure to organophosphate agents can produce long term central nervous system (CNS) effects. Ocinaplon and other pyrazolopyrimidines can be used to treat the seizures associated with exposure to organophosphorus nerve agents such as soman, tabun, VX and sarin, and can also be administered to individuals at risk for exposure to nerve agents prior to such exposure. Pyrazolopyrimidines therefore represent a new tool for treating and preventing the effects of exposure to organophosphate agents experienced by subjects.

The present method of treating exposure to an organophosphate compound comprises administering to a subject in need thereof a therapeutically effective amount of a pharmaceutical composition comprising a pyrazolopyrimidine compound. Preferably, the compound has the following formula:

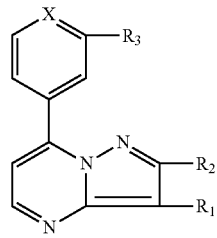

where:

X is C or N;

$R_1$ is selected from the group consisting of hydrogen, halogen, cyano, and

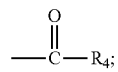

$R_2$ is selected from the group consisting of hydrogen and alkyl ($C_1$-$C_3$);

$R_3$ is selected from the group consisting of hydrogen and

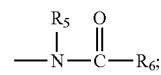

$R_4$ is selected from the group consisting of hydrogen, alkyl ($C_1$-$C_6$), alkoxy ($C_1$-$C_6$)

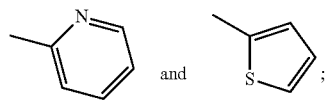

$R_5$ is selected from the group consisting of hydrogen, alkyl($C_1$-$C_6$), alkenyl($C_2$-$C_6$); and $R_6$ is selected from the group consisting of hydrogen, alkyl($C_1$-$C_6$), or a salt or ester thereof. $R_5$ and $R_6$ are methyl or ethyl, and the pyrazolopyrimidine compound is preferably ocinaplon, zaleplon, indiplon, and divaplon. The present composition also preferably comprises a pharmaceutically acceptable excipient in combination with the pyrazoloppimidine compound.

The present composition can be administered to a subject either following exposure of the subject to the organophosphate compound or prior to such exposure. If the administration occurs after exposure, the compound is preferably administered to the subject within one hour following exposure of the subject to the organophosphate compound, and more preferably within one to five minutes following exposure of the subject to the organophosphate compound.

DESCRIPTION

Definitions

As used herein, the following terms and variations thereof have the meanings given below, unless a different meaning is clearly intended by the context in which such term is used.

As used herein, the term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise.

A "derivative" of a compound refers to a compound that has been partially substituted or otherwise chemically modified by the addition, substitution, or deletion of one or more other chemical groups or components.

"Organophosphate" refers to compounds, specifically nerve agents, which are esters of phosphoric acid that act on the enzyme acetylcholinesterase and have neurotoxicity. Such compounds include the nerve agents tabun (Ethyl N,N-dimethylphosphoramidocyanidate, also referred to as GA), sarin (O-Isopropyl methylphosphonofluoridate, also referred to as GB), soman (O-Pinacolyl methylphosphonofluoridate, also referred to as GD), and VX (O-ethyl-S-[2 (diisopropylamino)ethyl]methylphosphonothiolate). Other organophosphate compounds include insecticides, such as phosphoric acid diethyl 4-nitrophenyl ester (paraoxon), diethyl-p-nitrophenyl monothiophosphate (parathion) and phosphorothioic acid O-(3-chloro-4-methyl-2-oxo-2H-1-benzopyran-7-yl)O,O-diethyl ester (coumaphos).

"Pyrazolopyrimidines" are nonbenzodiazepine drugs, including ocinaplon, zaleplon, indiplon, and divaplon, which are typified by linked six-sided (benzene) and sometimes five-sided rings (methylpyrazol), including the following chemical structures and derivatives thereof:

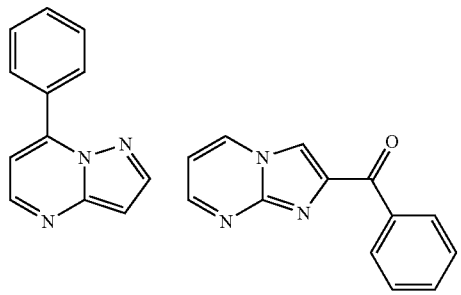

A "subject" refers to a mammal, preferably a human. This term can also refer however to an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

"Treat" and "treatment," with respect to the exposure of a subject to an organophosphate compound, refer to a medical intervention which attenuates, prevents, and/or counteracts the effects of such exposure. The foregoing terms can refer to the prophylactic administration of the present compounds and compositions to subjects at risk of exposure to an organophosphate compound prior to an anticipated exposure, and/or can refer to the administration of the present compounds and compositions following such exposure.

Compounds

The compounds of the present invention are pyrazolopyrimidines, such as ocinaplon, zaleplon, indiplon, and divaplon, and include derivatives of such pyrazolopyrimidines. A preferred pyrazolopyrimidine compound is ocinaplon, whose chemical name is pyridin-2-yl(7-(pyridin-4-yl)pyrazolo[1,5-a]pyrimidin-3-yl)methanone. Ocinaplon has the following chemical structure:

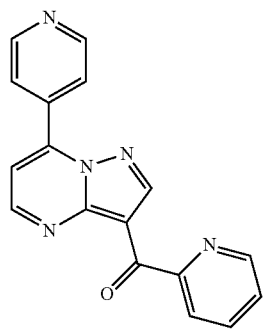 [SMILES: O=C(c1ccccn1)c1cnn2c(-c3ccncc3)ccnc12]

It is believed that ocinaplon modulates gamma-aminobutyrate (GABA) receptors, in particular $GABA_A$ receptors. Ocinaplon exhibits relatively few sedative or amnesic effects.

Another pyrazolopyrimidine compound is zaleplon (N-(3-(3-cyanopyrazolo[1,5-a]pyrimidin-7-yl)phenyl)-N-ethylacetamide), having the following chemical structure:

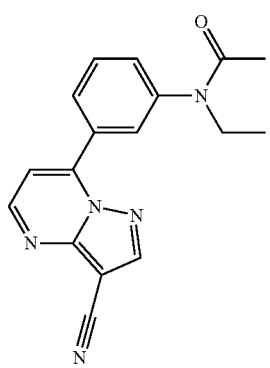 [SMILES: CCN(C(C)=O)c1cccc(-c2ccnc3c(C#N)cnn23)c1]

A further pyrazolopyrimidine compound is indiplon (N-methyl-N-[3-[3-(thiophene-2-carbonyl)pyrazolo[5,1-b]pyrimidin-7-yl]phenyl]acetamide), having the following chemical structure:

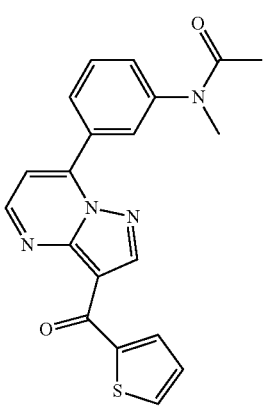 [SMILES: CC(=O)N(C)c1cccc(-c2ccnc3c(C(=O)c4cccs4)cnn23)c1]

Yet another pyrazolopyrimidine compound is divaplon ((6-ethyl-7-methoxy-5-methylimidazo[1,2-a]pyrimidin-2-yl)-phenylmethanone), having the following chemical structure:

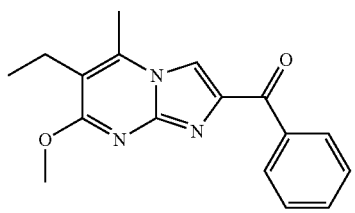 [SMILES: CCc1c(OC)nc2nc(C(=O)c3ccccc3)cn2c1C]

Compound Properties

In general, the present compounds include salts and prodrug esters of the compounds described herein. It is well known that organic compounds often comprise groups that can accept or donate protons, depending upon the pH of the solution in which they are present. These groups include carboxyl groups, hydroxyl groups, amino groups, sulfonic acid groups, and other groups known to be involved in acid-base reactions. The recitation of a compound in the present application includes such salt forms as occur at physiological pH or at the pH of a pharmaceutical composition unless specifically excluded.

Similarly, prodrug esters can be formed by reaction of either a carboxyl or a hydroxyl group on the compound with either an acid or an alcohol to form an ester. Typically, the acid or alcohol includes an alkyl group such as methyl, ethyl, propyl, isopropyl, butyl, isobutyl, and tertiary butyl. These groups can be substituted with substituents such as hydroxy, halo, or other substituents. Such prodrugs are well known in the art. The prodrug is converted into the active compound by hydrolysis of the ester linkage, typically by intracellular enzymes. Other suitable groups that can be used to form prodrug esters are well known in the art.

Synthesis

Methods of synthesizing pyrazolopyrimidines, including ocinaplon, are known to those of skill in the art. Methods for making ocinaplon are disclosed, inter alia, in U.S. Pat. No. 4,521,422 and in U.S. Patent Publication No. 20080045547. Another synthetic method is as follows:

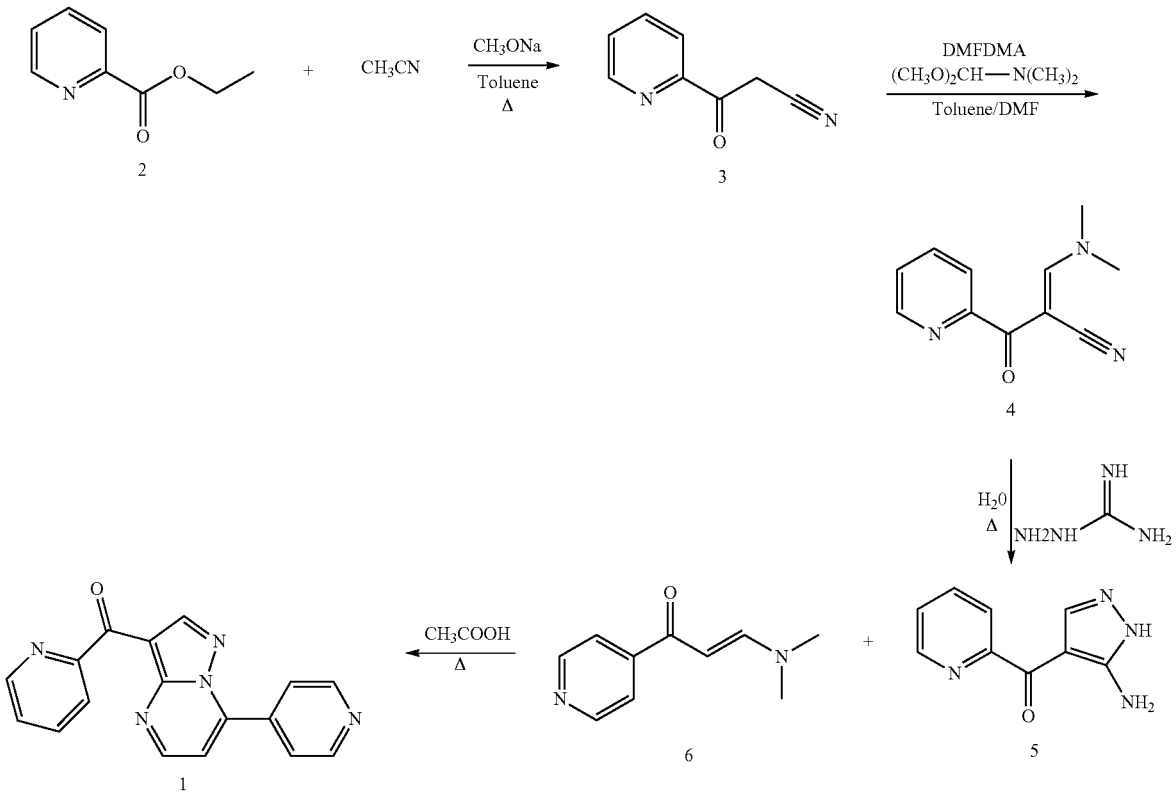

In the foregoing synthetic scheme, 2-ethylpicolinate is converted into pyridylcarbonylacetonitrile, which then reacts with dimethylformamide dimethylacetal (DMFDMA) to form compound 4. Compound 4 reacts with aminoguanidine to afford compound 5. The condensation of the aminopyrazole 5 with compound 6 provide ocinaplon 1. Compound 6 can be prepared from 4-pyridylcarboxylic acid via 4-acetylpyridine as follows:

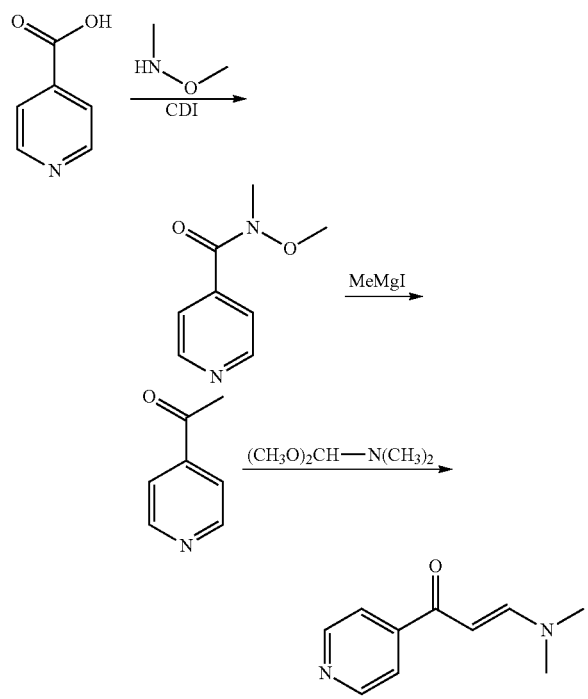

Persons having ordinary skill in the art of medicinal and/or organic chemistry will understand that other starting materials, intermediates, and reaction conditions are possible. Furthermore, it is understood that various salts and esters of these compounds can be made and that these salts and esters can have a biological activity similar or equivalent to the parent compound, such as the HCl, HBr and Bisulfate salts of ocinaplon disclosed in U.S. Patent Publication No 20080045547. Synthetic processes for producing zaleplon and indiplon are also known to the art, for example, in U.S. Pat. No. 4,626,538 (zaleplon), and U.S. Pat. No. 6,399,621 (indiplon).

Pharmaceutical Compositions

A pharmaceutical composition can comprise one or more of the present compounds. Such a composition preferably comprises: (1) a therapeutically effective amount of one or more of the present compounds (and/or salts and esters thereof); and (2) a pharmaceutically acceptable excipient.

A pharmaceutically acceptable excipient, including carriers, can be chosen from those generally known in the art including, but not limited to, inert solid diluents, aqueous solutions, or non-toxic organic solvents, depending on the route of administration. If desired, these pharmaceutical formulations can also contain preservatives and stabilizing agents and the like, for example substances such as, but not limited to, pharmaceutically acceptable excipients selected from the group consisting of wetting or emulsifying agents, pH buffering agents, human serum albumin, antioxidants, preservatives, bacteriostatic agents, dextrose, sucrose, trehalose, maltose, lecithin, glycine, sorbic acid, propylene glycol, polyethylene glycol, protamine sulfate, sodium chloride, or potassium chloride, mineral oil, vegetable oils and combinations thereof. Those skilled in the art will appreciate that other carriers can also be used.

Liquid compositions can also contain liquid phase excipients either in addition to or to the exclusion of water. Examples of such additional liquid phases are glycerin, vegetable oils such as cottonseed oil, organic esters such as ethyl oleate, and water-oil emulsions.

Formulations suitable for parenteral administration, such as, for example, by intravenous, intramuscular, intradermal, and subcutaneous routes, include aqueous and non-aqueous isotonic sterile injection solutions. These can contain antioxidants, buffers, preservatives, bacteriostatic agents, and solutes that render the formulation isotonic with blood. Alternatively, these formulations can be aqueous or non-aqueous sterile suspensions that can include suspending agents, thickening agents, solubilizers, stabilizers, and preservatives. The pharmaceutical compositions of the present invention can be formulated for administration by intravenous infusion, oral, topical, intraperitoneal, intravesical, transdermal, intranasal, rectal, vaginal, intramuscular, intradermal, subcutaneous and intrathecal routes.

Formulations of the present compounds can be presented in unit-dose or multi-dose sealed containers, in physical forms such as ampules or vials. The compositions can also be made into aerosol formations (i.e., they can be "nebulized") to be administered via inhalation. Aerosol formulations can be placed into pressurized acceptable propellants, such as dichloromethane, propane, or nitrogen. Other suitable propellants are known in the art.

Preclinical Models and Clinical Evaluation

In order to screen for the most effective of the present compounds and pharmaceutical compositions and determine appropriate candidates for further development, as well as to determine appropriate dosages of such compounds and compositions for a human subject, preclinical animal models can be used. Exemplary animal models are set forth below, although it is within the ability of one of skill in the art to select and use an appropriate model for treating the effects of exposure to nerve agents.

Preferably, a series of tests is performed in animal models to screen for the activity of the present compounds to treat the effects of exposure to nerve agents. Preliminary screening tests can be used to determine appropriate dosages to test in follow-on models. Appropriately selected doses of compounds and compositions tested in this way can then be subjected to testing for efficacy against nerve agent exposure.

A. Models for Determining Appropriate Dosages

1. Neuromuscular Coordination Model (Rotarod)

This model can be used to determine the dose of a compound or composition at which unwanted side effects (muscle tone/motor coordination deficits) occur. Animals (C57 Mice) are placed on a rotarod treadmill (model V EE/85, Columbus Instruments, Columbus, Ohio) accelerating from 1 to 80 revolutions/4 minutes. All mice are given two control trials at least 12 hours before administration of a compound. Mice are tested on the rotarod 30 minutes after administration of the compound. The number of seconds each mouse remained on the rotarod is recorded.

Doses at which the coordination of an animal is decreased or at which its motor function is altered, such that the ability of the animal to remain on the rotarod is reduced, are determined Doses below this are selected for further evaluation.

2. Spontaneous Activity Model (Locomotor Activity)

Ambulatory and non-ambulatory activity can be used to test spontaneous and drug-induced motor activity. The test can be used to profile the potential for a drug to induce hyperactivity or sedation.

In this model, Kinder Scientific photobeam activity monitors are used to record the ambulatory and non-ambulatory motor activity. The monitors track the photobeam breaks made by the animal that are used to calculate the number of ambulatory and fine (non-ambulatory) motor movements. A drug-induced increase in activity can indicate the potential for an adverse event such as hyperactivity. A drug-induced decrease in response can indicate the potential for an adverse event such as sedation. Doses at which no significant change in activity are recorded, and more preferably at which no change in activity are recorded, can be selected for further evaluation.

3. Potentiated Startle (Anxiety Model)

This model can be used to evaluate anxiolytic or anxiogenic effects of a candidate molecule. In this model, Hamilton-Kinder startle chambers can be used for conditioning sessions and for the production and recording of startle responses. A classical conditioning procedure is then used to produce potentiation of startle responses. On the first of 2 days, rats, preferably Long Evans rats, are placed into dark startle chambers having shock grids. Following a 5-minute acclimation period, each rat is administered a 1 mA electric shock (500 ms) preceded by a 5 second presentation of light (15 watt) which remains on for the duration of the shock. Ten presentations of the light and shock are given in each conditioning session.

The rats are then administered a test compound, after which startle testing sessions are conducted. A block of 10 consecutive presentations of acoustic startle stimuli (110 dB, non-light-paired) are presented at the beginning of the session in order to minimize the influences of the initial rapid phase of habituation to the stimulus. This is followed by 20 alternating trials of the noise alone or noise preceded by the light. Excluding the initial trial block, startle response amplitudes for each trial type (noise–alone vs. light+noise) are averaged for each rat across the entire test session.

Compounds and compositions appropriate development preferably do not result in either anxiogenic or anxiolytic activity.

B. Seizure Models

Models for evaluating the effectiveness of the present compounds in treating seizures and other effects of exposure to organophosphate nerve agents can be identified and/or developed by one of skill in the art. The present compounds can be screened for their effectiveness in treating seizures, for example, in a lithium-pilocarpine-induced model of seizures. The injection of pilocarpine, a muscarinic agonist, induces generalized convulsive seizures in rodents. When rats are pretreated with lithium chloride, the seizures can be produced by a substantially lower dose of pilocarpine.

In the lithium-pilocarpine model, lithium chloride (3 mEq/kg i.p.) is first administered to adult male Sprague-Dawley rats. On the following day, methylscopolamine bromide (1 mg/kg s.c.) is administered to limit the peripheral effects of the convulsant. Pilocarpine hydrochloride (25 mg/kg s.c.) is then administered 30 min after methylscopolamine.

A compound of the present invention is then administered to the pilocarpine-treated rats 1 hour after the onset of seizures. A control group receives lithium, saline and vehicle instead of pilocarpine and the compound being tested. The effect of the compound in treating seizures can be evaluated by behavioral observation of the tested animals, by recording bilateral EEG cortical activity, and/or by recording unilateral EEG hippocampal activity.

C. Clinical Development

Following the testing of candidate compounds and/or compositions in preclinical animal models, candidates for further development can be selected based on the criteria set forth above. One or more selected candidates having desirable preclinical profiles can then be subjected to clinical evaluation in human subjects using methods known to those of skill in the art.

Treatments

The effects of nerve agent exposure can be treated by administering therapeutically effective amounts of one or more of the present compounds and/or pharmaceutical compositions to a subject in need thereof. The present compounds and/or compositions are administered to a subject in a quantity sufficient to treat or prevent one or more symptoms associated with nerve agent exposure in the subject. The present compounds can also be administered in combination with other agents known to be useful in the treatment of nerve agent exposure, such as atropine sulfate, diazepam, and pralidoxime (2-PAM), either in physical combination or in combined therapy through the administration of the present compounds and agents in succession (in any order).

Administration of the present compounds and compositions can begin immediately following exposure to an organophosphate nerve agent, preferably within the first hour or first two hours following exposure, and more preferably within one to five minutes. Administration of the compositions and compounds can alternatively begin prior to an anticipated exposure (such as impending combat), in order to prevent or reduce the impact of subsequent exposure. The present invention thus includes the use of the present compounds and/or a pharmaceutical compositions prophylactically as well as following exposure to a nerve agent.

Depending upon the particular needs of the individual subject involved, the present compounds can be administered in various doses to provide effective treatments for nerve agent exposure. Factors such as the activity of the selected compound, half life of the compound, the physiological characteristics of the subject, the extent or nature of the subject's exposure or condition, and the method of administration will determine what constitutes an effective amount of the selected compounds. Generally, initial doses will be modified to determine the optimum dosage for treatment of the particular subject. The compounds can be administered using a number of different routes including oral administration, topical administration, transdermal administration, intraperitoneal injection, or intravenous injection directly into the bloodstream. Effective amounts of the compounds can also be administered through injection into the cerebrospinal fluid or infusion directly into the brain, if desired.

An effective amount of any embodiment of the present invention is determined using methods known to pharmacologists and clinicians having ordinary skill in the art. For example, the animal models described herein can be used to determine applicable dosages for a subject. As known to those of skill in the art, a very low dose of a compound, i.e. one found to be minimally toxic in animals (e.g., $\frac{1}{10} \times LD10$ in mice), can first be administered to a subject, and if that dose is found to be safe, the subject can be treated at a higher dose. A therapeutically effective amount of one of the present compounds for treating nerve agent exposure can then be determined by administering increasing amounts of such compound to a subject suffering from such exposure until such time as the subject's symptoms are observed or are reported by the subject to be diminished or eliminated.

In a preferred embodiment, the present compounds and compositions selected for use in treating nerve agent exposure have a therapeutic index of approximately 2 or greater. The therapeutic index is determined by dividing the dose at which adverse side effects occur by the dose at which efficacy for the condition is determined. A therapeutic index is preferably determined through the testing of a number of subjects. Another measure of therapeutic index is the lethal dose of a drug for 50% of a population ($LD_{50}$, in a preclinical model) divided by the minimum effective dose for 50% of the population ($ED_{50}$).

Blood levels of the present compounds can be determined using routine biological and chemical assays and these blood levels can be matched to the route of administration and half life of a selected compound. The blood level and route of administration can then be used to establish a therapeutically effective amount of a pharmaceutical composition comprising one of the present compounds for treating nerve agent exposure.

Exemplary dosages in accordance with the teachings of the present invention for these compounds range from 0.0001 mg/kg to 60 mg/kg, though alternative dosages are contemplated as being within the scope of the present invention. Suitable dosages can be chosen by the treating physician by taking into account such factors as the size, weight, age, and sex of the subject, the physiological state of the subject, the severity of the condition for which the compound is being administered, the response to treatment, the type and quantity of other medications being given to the subject that might interact with the compound, either potentiating it or inhibiting it, and other pharmacokinetic considerations such as liver and kidney function.

Suitable effective unit dosage amounts of ocinaplon for mammalian subjects preferably range from about 0.05 mg/kg to about 15 mg/kg per day, 0.1 mg/kg to about 12.5 mg/kg per day, 0.25 mg/kg to about 10 mg/kg per day, 0.5 mg/kg to about 7.5 mg/kg per day, 0.75 mg/kg to about 5 mg/kg per day or 1 mg/kg to about 5 mg/kg per day. Total amounts administered preferably range from about 1.25 mg to about 400 mg, about 2.5 mg to about 300 mg, about 5.0 mg to about 200 mg, about 10 mg to about 100 mg, or about 15 mg to about 50 mg. In certain embodiments, the effective unit dosage will be selected within narrower ranges of, for example, about 2.5 mg to about 10 mg, about 10 mg to about 50 mg, about 50 mg to about 100 mg, about 100 mg to about 200 mg, about 200 mg to about 300 mg or about 300 mg to about 400 mg.

Although the present invention has been discussed in considerable detail with reference to certain preferred embodiments, other embodiments are possible. The steps disclosed for the present methods are not intended to be limiting nor are they intended to indicate that each step is necessarily essential to the method, but instead are exemplary steps only. Therefore, the scope of the appended claims should not be limited to the description of preferred embodiments contained in this disclosure. All references cited herein are incorporated by reference in their entirety.

What is claimed is:

1. A method of treating exposure to sarin, comprising the step of administering to a subject in need thereof a therapeutically effective amount of a pharmaceutical composition comprising ocinaplon.

2. The method of claim 1, wherein the composition comprises a pharmaceutically acceptable excipient in combination with the ocinaplon.

3. The method of claim 1, wherein the composition is administered by an administrative route selected from the group consisting of intravenous, oral, topical, intraperitoneal, intravesical, transdermal, nasal, rectal, vaginal, intramuscular, intradermal, subcutaneous and intrathecal.

4. The method of claim 1, wherein the therapeutically effective amount of the composition is administered to the subject following exposure of the subject to sarin.

5. The method of claim 4, wherein the composition is administered to the subject within one hour following exposure of the subject to sarin.

6. The method of claim 5, wherein the composition is administered to the subject within five minutes following exposure of the subject to sarin.

7. The method of claim 6, wherein the composition is administered to the subject within one minute following exposure of the subject to sarin.

8. The method of claim 1, wherein the therapeutically effective amount of the composition is administered to the subject prior to exposure of the subject to sarin.

* * * * *